(12) United States Patent
Warner et al.

(10) Patent No.: US 9,102,581 B2
(45) Date of Patent: *Aug. 11, 2015

(54) PROCESS FOR PRODUCING ETHANOL USING AN EXTRACTIVE DISTILLATION COLUMN

(71) Applicant: Celanese International Corporation, Irving, TX (US)

(72) Inventors: R. Jay Warner, Houston, TX (US); Radmila Wollrab, Pasadena, TX (US); Wael Amleh, Pearland, TX (US); Gerald Grusendorf, Rosharon, TX (US); Trinity Horton Hale, Houston, TX (US); Victor J. Johnston, Houston, TX (US); Fred Ronaold Olsson, Corpus Christi, TX (US); Nathan Kirk Powell, Waxahachie, TX (US); Manuel Salado, Seabrook, TX (US); Lincoln Sarager, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/644,763

(22) Filed: Oct. 4, 2012

(65) Prior Publication Data

US 2013/0053606 A1    Feb. 28, 2013

Related U.S. Application Data

(63) Continuation of application No. 12/852,305, filed on Aug. 6, 2010, now Pat. No. 8,304,587.

(60) Provisional application No. 61/332,696, filed on May 7, 2010, provisional application No. 61/332,699, filed on May 7, 2010, provisional application No. 61/332,728, filed on May 7, 2010, provisional application No. 61/346,344, filed on May 19, 2010.

(51) Int. Cl.
*C07C 29/149*    (2006.01)
*C07C 29/09*    (2006.01)

(52) U.S. Cl.
CPC .............. *C07C 29/095* (2013.01); *C07C 29/149* (2013.01)

(58) Field of Classification Search
CPC ..................................................... C07C 29/149
USPC ........................................ 568/885, 913, 918
See application file for complete search history.

(56) References Cited

U.S. PATENT DOCUMENTS

| | | |
|---|---|---|
| 2,649,407 A | 8/1953 | Harrison et al. |
| 2,702,783 A | 2/1955 | Harrison et al. |
| 2,744,939 A | 5/1956 | Kennel |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,149,940 A | 4/1979 | Pinto |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,569,726 A | 2/1986 | Berg et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |

(Continued)

FOREIGN PATENT DOCUMENTS

| | | |
|---|---|---|
| EP | 0104197 | 4/1984 |
| EP | 0137749 | 4/1985 |

(Continued)

OTHER PUBLICATIONS

Udeye, et al., "Ethanol heterogeneous azeotropic distillation design and construction", International Journal of Physical Sciences, vol. 4 (3), Mar. 2009, pp. 101-106.

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

(Continued)

*Primary Examiner* — Elvis O Price
(74) *Attorney, Agent, or Firm* — Kilpatrick Townsend & Stockton LLP

(57) ABSTRACT

Recovery of ethanol from a crude ethanol product obtained from the hydrogenation of acetic acid. Separation and purification processes of crude ethanol product are employed to allow recovery of ethanol and remove impurities. In addition, the process involves separating the crude ethanol product using an extractive distillation column that employs an extraction agent, such as a recycled stream comprising water.

20 Claims, 3 Drawing Sheets

(56) References Cited

U.S. PATENT DOCUMENTS

| | | |
|---|---|---|
| 4,804,791 A | 2/1989 | Kitson et al. |
| 4,826,795 A | 5/1989 | Kitson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,215,902 A | 6/1993 | Tedder |
| 5,233,099 A | 8/1993 | Tabata et al. |
| 5,237,108 A | 8/1993 | Marraccini et al. |
| 5,250,271 A | 10/1993 | Horizoe et al. |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Gaddy et al. |
| 5,993,610 A | 11/1999 | Berg |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 | 4/2002 | Nieuwoudt et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,809,217 B1 | 10/2004 | Colley et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,115,772 B2 | 10/2006 | Picard et al. |
| 7,208,624 B2 | 4/2007 | Scates et al. |
| 7,297,236 B1 | 11/2007 | Vander Griend et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,744,727 B2 | 6/2010 | Blum et al. |
| 2006/0019360 A1 | 1/2006 | Verser et al. |
| 2006/0127999 A1 | 6/2006 | Verser et al. |
| 2007/0031954 A1 | 2/2007 | Mairal et al. |
| 2007/0270511 A1 | 11/2007 | Melnichuk et al. |
| 2008/0135396 A1 | 6/2008 | Blum |
| 2009/0014313 A1 | 1/2009 | Lee et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Weiner et al. |
| 2010/0185021 A1 | 7/2010 | Ross et al. |
| 2010/0197485 A1 | 8/2010 | Johnston et al. |
| 2011/0004033 A1 | 1/2011 | Johnston et al. |
| 2011/0082322 A1 | 4/2011 | Jevtic et al. |
| 2012/0273338 A1 | 11/2012 | Lee |
| 2012/0323049 A1 | 12/2012 | Lee |
| 2012/0323050 A1 | 12/2012 | Lee |

FOREIGN PATENT DOCUMENTS

| | | |
|---|---|---|
| EP | 0167300 | 1/1986 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | S61-183237 A | 8/1986 |
| JP | S61-243033 A | 10/1986 |
| JP | H06-25033 A | 2/1994 |
| WO | WO 83/03409 | 10/1983 |
| WO | WO 2007/003897 | 1/2007 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2009/105860 | 9/2009 |
| WO | WO 2010/014151 | 2/2010 |
| WO | WO 2010/055285 | 5/2010 |
| WO | WO 2011/053365 | 5/2011 |

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

International Preliminary Report on Patentability for PCT/US2011/023328 mailed Jun. 25, 2012.

International Written Opinion for PCT/US2011/023328 mailed May 8, 2012.

International Search Report and Written Opinion for PCT/US2011/023328 mailed Aug. 5, 2011.

Response to Final Office Action for U.S. Appl. No. 13/162,005, filed Nov. 26, 2013.

Response to Final Office Action for U.S. Appl. No. 13/162,034, filed Nov. 27, 2013.

Office Action for corresponding Chinese Appl. No. 201180001870.5 dated Aug. 5, 2014.

Japanese Office Action mailed on Dec. 15, 2014 for JP Patent Application No. 2012-551384, with English translation, 7 pages.

PROCESS FOR PRODUCING ETHANOL USING AN EXTRACTIVE DISTILLATION COLUMN

CROSS REFERENCE TO RELATED APPLICATION

This application is a continuation of Ser. No. 12/852,305, filed Aug. 6, 2010, which claims priority to U.S. Provisional Application No. 61/332,699, filed on May 7, 2010, U.S. Provisional Application No. 61/332,728, filed on May 7, 2010; and U.S. Provisional Application No. 61/346,344, filed on May 19, 2010, the entire contents and disclosures of which are incorporated herein by reference.

FIELD OF THE INVENTION

The present invention relates generally to processes for producing ethanol and, in particular, to processes for producing ethanol from the hydrogenation of acetic acid.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

Therefore, a need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for purifying a crude ethanol product, the process comprising hydrogenating an acetic acid feed stream in a reactor in the presence of a catalyst to form a crude ethanol product; separating at least a portion of the crude ethanol product in a first column into a first distillate comprising ethanol, water and ethyl acetate, and a first residue comprising acetic acid; separating at least a portion of the first distillate in a second column into a second distillate comprising ethyl acetate and a second residue comprising ethanol and water, wherein the second column is an extractive distillation column; feeding an extraction agent to the second column; and separating at least a portion of the second residue in a third column into a third distillate comprising ethanol and a third residue comprising water.

In a second embodiment, the present invention is directed to a process for purifying a crude ethanol product, the process comprising hydrogenating an acetic acid feed stream in a reactor in the presence of a catalyst to form a crude ethanol product; separating at least a portion of the crude ethanol product in a first column into a first distillate comprising ethanol, water and ethyl acetate, and a first residue comprising acetic acid; separating at least a portion of the first distillate in a second column into a second distillate comprising ethyl acetate and a second residue comprising ethanol and water; and separating at least a portion of the second residue in a third column into a third distillate comprising ethanol and a third residue comprising water; wherein at least a portion of the third residue is directly or indirectly returned to the second column.

In a third embodiment, the present invention is directed to a process for purifying a crude ethanol product comprising ethanol, water, acetic acid, acetaldehyde and ethyl acetate, the process comprising separating the crude ethanol product in a first column into a first distillate comprising ethanol, water and ethyl acetate, and a first residue comprising acetic acid; separating the first distillate in a second column into a second distillate comprising ethyl acetate and a second residue comprising ethanol and water; separating the second residue in a third column into a third distillate comprising ethanol and a third residue comprising water; and directing at least a portion of the third residue to the second column.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
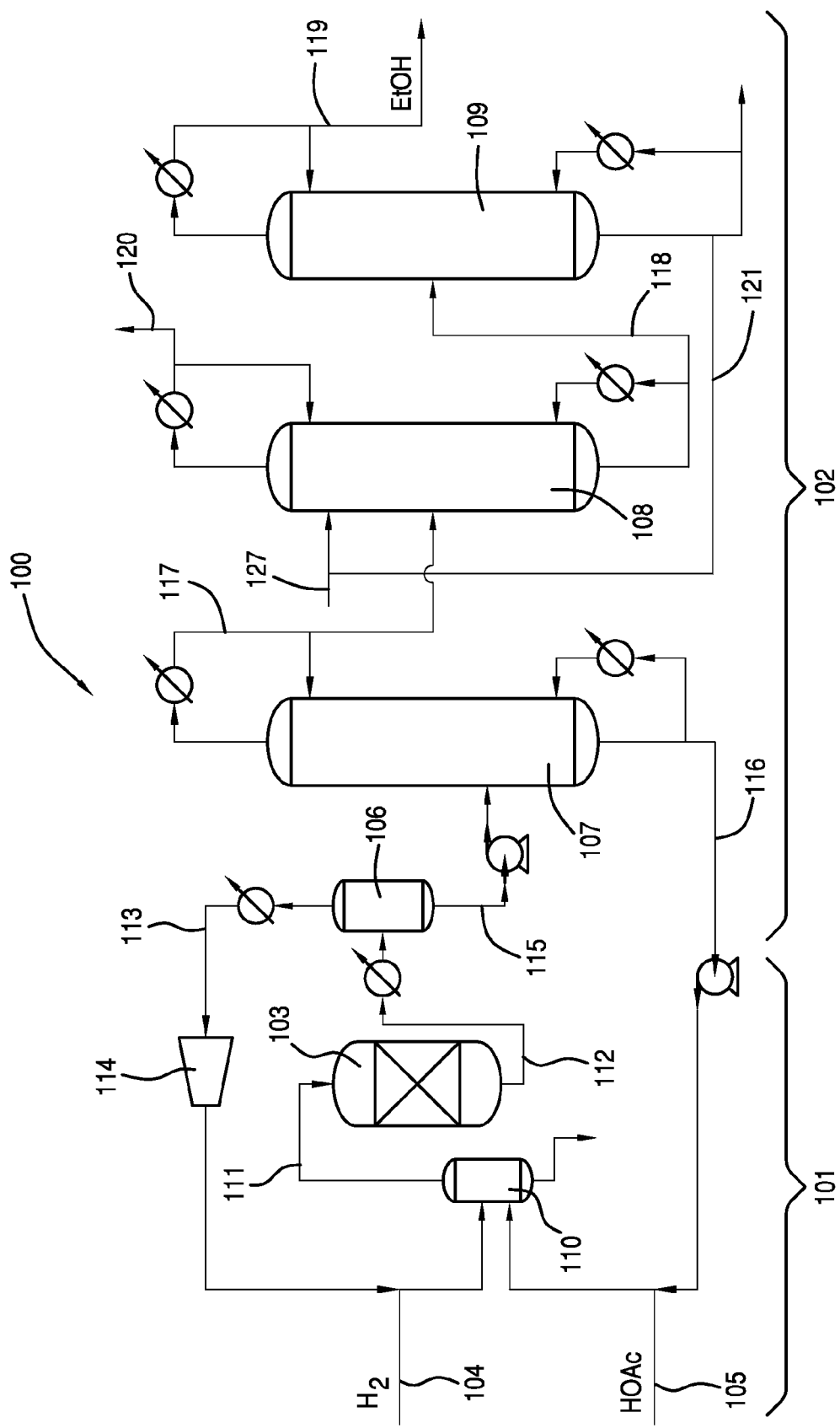
FIG. 1 is a schematic diagram of a hydrogenation system in accordance with one embodiment of the present invention.

The present invention relates to processes for recovering ethanol from a crude ethanol product. In particular, the present invention relates to processes for recovering and/or purifying ethanol from a crude ethanol product, which preferably is formed in a process for hydrogenating acetic acid in the presence of a catalyst.

Since binary and ternary azeotropes may form between two or more of ethyl acetate, ethanol and water in the crude ethanol product or a processed stream thereof, the process optionally employs an extractive distillation column to facilitate separation of these components. In these embodiments, ethanol advantageously may be separated from the crude ethanol product even when the content of ethyl acetate and/or water in the crude ethanol product is sufficient to form such azeotropes. The extraction agent employed in the extractive distillation column may comprise water obtained from an external source, from a portion of a recycled stream within the process, or combinations thereof. The extraction agent employed in the extractive distillation column preferably comprises a recycled stream from a column that separates ethanol from water. Preferably, the extraction agent comprises at least a portion of the residue from this column, which preferably comprises water. Embodiments of the present invention beneficially may be used in applications for recovery and/or purifying of ethanol on an industrial scale.

Without being bound to theory, it is believed that the recycled stream comprising the extraction agent further promotes the separation in the extractive distillation column. In addition, the recycled stream may also promote the separation of ethanol from the crude ethanol product. In one embodiment, the process of the present invention may improve efficiency and reduce cost by decrease water use and consumption. In addition, such embodiments may advantageously reduce waste generation. In another embodiment, the process of the present invention may use the recycle water to integrate the heat throughout the system and reduce energy consumption.

In one embodiment, the process further includes a step of separating acetaldehyde from the crude ethanol product and returning separated acetaldehyde to the reaction process, preferably to the acetic acid feed, to the vaporizer, or to the hydrogenation reactor. The returned acetaldehyde may be reacted under the hydrogenation conditions. In one embodiment, the acetaldehyde is separated from a stream comprising ethyl acetate derived from the crude ethanol product. This may allow a major portion of the ethyl acetate to be removed from the process without building up ethyl acetate throughout the separation process.

Hydrogenation Process

The hydrogenation of acetic acid to form ethanol and water may be represented by the following reaction:

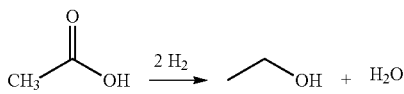

Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication No. 2010/0029995, the entireties of which are incorporated herein by reference. Additional catalysts are described in U.S. application Ser. No. 12/698,968, entitled "Catalysts for Making Ethanol from Acetic Acid," filed on Feb. 2, 2010, the entirety of which is incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication No. 2010/0029995, and U.S. application Ser. No. 12/698,968, referred to above, the entireties of which are incorporated herein by reference.

Some embodiments of the process of hydrogenating acetic acid to form ethanol according to one embodiment of the invention may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosure of which is incorporated herein by reference.

Optionally, the production of ethanol may be integrated with such methanol carbonylation processes.

United States Patent No. RE 35,377 also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the present of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 per kilogram catalyst per hour or from 600 to 2,000 per kilogram catalyst per hour.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %. Ethyl acetate may also be produced during the hydrogenation of acetic acid or through side reactions and may be present, for example, in amounts ranging from 0 to 20 wt. %, e.g., from 0 to 15 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Purification

FIG. 1 shows a hydrogenation system 100 suitable for the hydrogenation of acetic acid and separating ethanol from the crude reaction mixture according to one embodiment of the invention. System 100 comprises reaction zone 101 and distillation zone 102. Reaction zone 101 comprises reactor 103, hydrogen feed line 104 and acetic acid feed line 105. Distillation zone 102 comprises flasher 106, first column 107, second column 108, and third column 109. As shown in FIG. 1, a portion or all of third residue in line 121 from the third column 109 preferably is recycled to the second column 108. Although FIG. 1 illustrates the third residue being directly recycled to the second column, in other embodiments the third residue may be stored in a holding tank and indirectly recycled to the second column. In still other embodiments, only a portion, e.g., an aliquot portion, of the third residue is recycled, directly or indirectly, to the second column. It is also possible to utilize water from another source via line 127 to replace a portion or all of the third residue that may be fed to the second column as the extraction agent.

Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1, and may be recycled thereto. In addition, although FIG. 1 shows line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 KPa to 2000 KPa, e.g., from 75 KPa to 1500 KPa or from 100 to 1000 KPa. In one preferred embodiment the temperature and pressure of the flasher is similar to the temperature and pressure of the reactor 103.

The vapor stream exiting the flasher may comprise hydrogen and hydrocarbons, which may be purged and/or returned to reaction zone 101 via line 113. As shown in FIG. 1, the returned portion of the vapor stream passes through compressor 114 and is combined with the hydrogen feed and co-fed to vaporizer 110.

The liquid from flasher 106 is withdrawn and pumped via line 115 to the side of first column 107, also referred to as the acid separation column. In one embodiment, the contents of line 115 may be substantially similar to the crude ethanol product obtained from the reactor, except that the composition has substantially no hydrogen, carbon dioxide, methane or ethane, which are removed by the flasher 106. Exemplary components of liquid in line 115 are provided in Table 2. It should be understood that liquid line 115 may contain other components, not listed, such as components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in line 115 is less than 5 wt. %, the acid separation column 107 may be skipped and line 115 may be introduced directly to second column 108, also referred to herein as a light ends column.

In the embodiment shown in FIG. 1, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. Recycling the acetic acid in line 116 to the vaporizer 110 may reduce the amount of heavies that need to be purged from vaporizer 110. Reducing the amount of heavies to be purged may improve efficiencies of the process while reducing byproducts.

First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Figure 2:
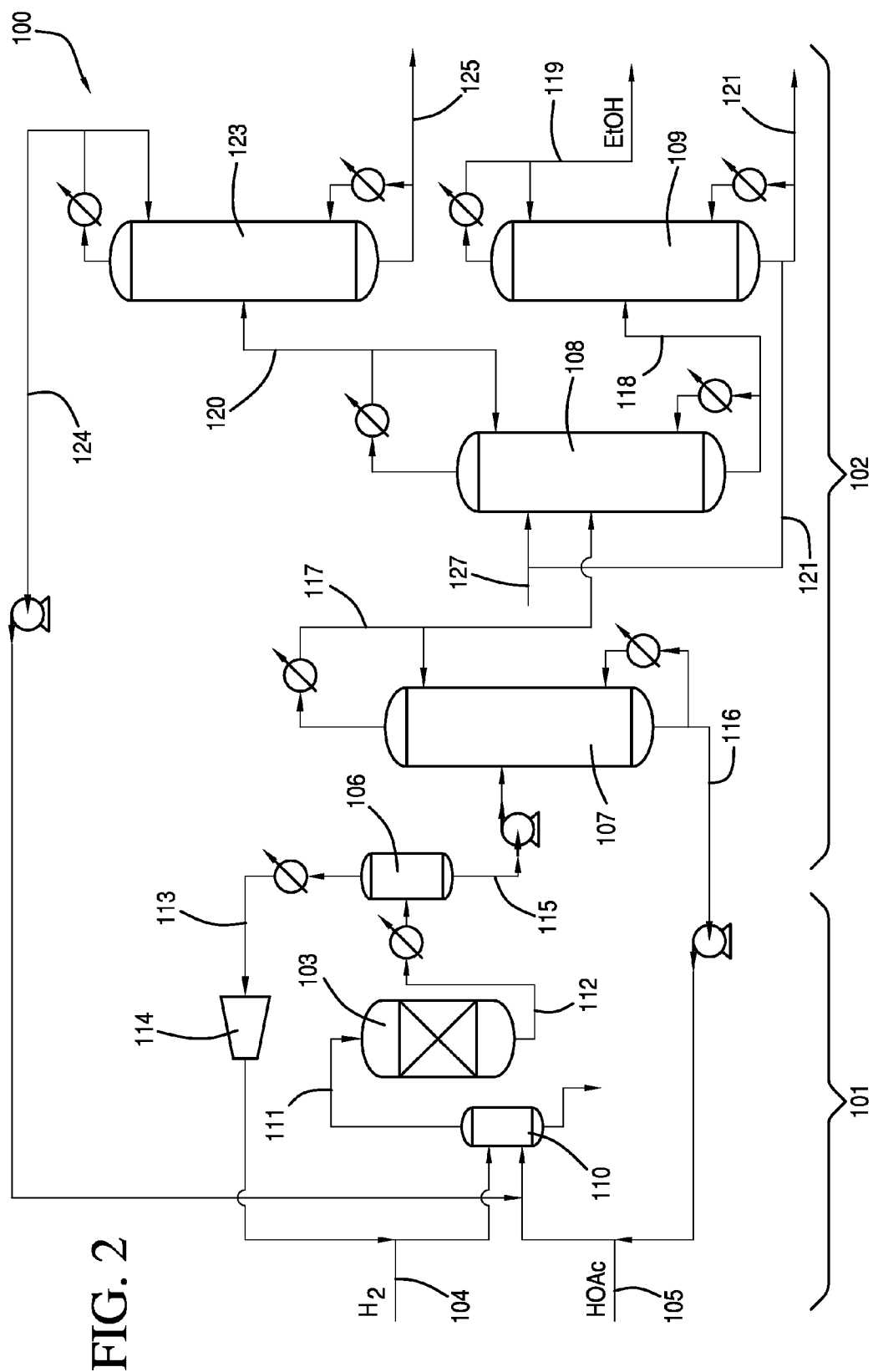
FIG. 2 is a schematic diagram of a hydrogenation system in accordance with another embodiment of the present invention.

Any of columns 107, 108, 109, or 123 in FIG. 2, may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1 and 2. As shown in FIGS. 1 and 2, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and flasher are shown in FIGS. 1 and 2, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 110° C. to 117° C. or from 111° C. to 115° C. The temperature of the distillate exiting in line 117 from column 107 preferably is from 70° C. to 110° C., e.g., from 75° C. to 95° C. or from 80° C. to 90° C. Column 107 preferably operates at ambient pressure. In other embodiments, the pressure of first column 107 may range from 0.1 KPa to 510 KPa, e.g., from 1 KPa to 475 KPa or from 1 KPa to 375 KPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increase from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes.

The first distillate in line 117 is introduced to the second column 108, also referred to as the "light ends column," preferably in the middle part of column 108, e.g., middle half or middle third. Preferably the second column 108 is an extractive distillation column, and an extraction agent is added thereto via lines 121 and/or 127. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As indicated above, the first distillate in line 117 that is fed to the second column 108 comprises ethyl acetate, ethanol, and water. These compounds tend to form binary and ternary azeotropes, which decrease separation efficiency. As shown, in one embodiment the extraction agent comprises the third residue in line 121. Preferably, the recycled third residue in line 121 is fed to second column 108 at a point higher than the first distillate in line 117. In one embodiment, the recycled third residue in line 121 is fed near the top of second column 108 or fed, for example, above the feed in line 117 and below the reflux line from the condensed overheads. In a tray column, the third residue in line 121 is continuously added near the top of the second column 108 so that an appreciable amount of the third residue is present in the liquid phase on all of the trays below. In another embodiment, the extraction agent is fed from a source outside of the process 100 via line 127 to second column 108. Preferably this extraction agent comprises water.

Figure 3:
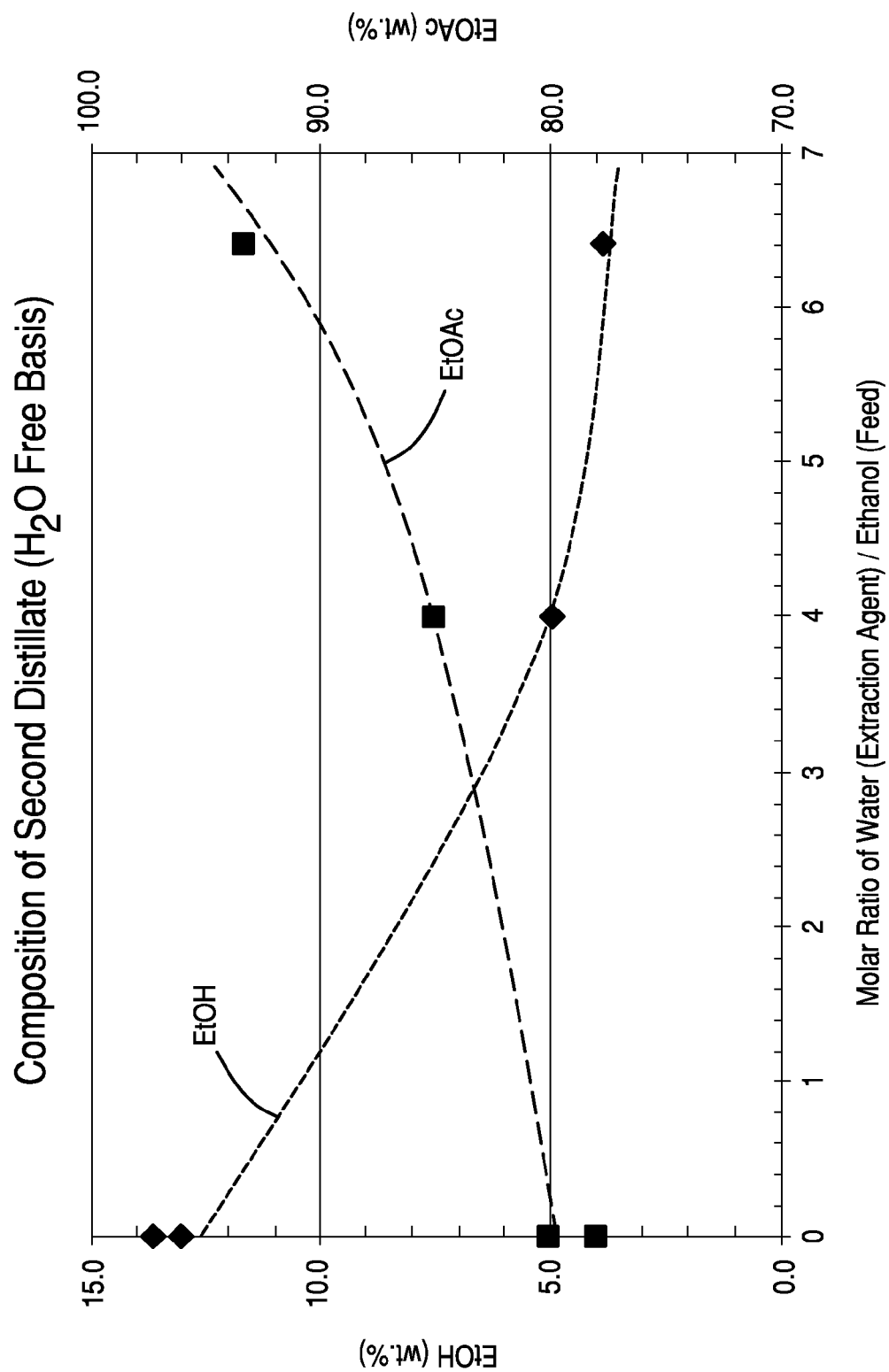
FIG. 3 is a graph of the ethanol and ethyl acetate concentration changes in the second distillate with the addition of an extraction agent to the second column.

The molar ratio of the water in the extraction agent to the ethanol in the feed to the second column is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate, as shown in FIG. 3.

In one embodiment, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 108. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 121 and co-fed to the second column 108. The additional extraction agent may also be added separately to the second column. In one aspect, the extraction agent comprises an extraction agent, e.g., water, derived from an external source via line 127 and none of the extraction agent is derived from the third residue.

Second column 108 may be a tray or packed column. In one embodiment, second column 108 is a tray column having from 5 to 70 trays, e.g., from 15 to 50 trays or from 20 to 45 trays.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

| SECOND COLUMN | | | |
|---|---|---|---|
| | Conc. (wt. %) | Conc. (wt. %) | Conc. (wt. %) |
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Acetal | <5 | 0.001 to 2 | 0.01 to 1 |
| Residue | | | |
| Water | 30 to 90 | 40 to 85 | 50 to 85 |
| Ethanol | 10 to 75 | 15 to 60 | 20 to 50 |
| Ethyl Acetate | <3 | 0.001 to 2 | 0.001 to 0.5 |
| Acetic Acid | <0.5 | 0.001 to 0.3 | 0.001 to 0.2 |

In preferred embodiments, the recycling of the third residue promotes the separation of ethyl acetate from the residue of the second column 108. For example, the weight ratio of ethyl acetate in the second residue to second distillate preferably is less than 0.4:1, e.g., less than 0.2:1 or less than 0.1:1. In embodiments that use an extractive distillation column with water as an extraction agent as the second column 108, the weight ratio of ethyl acetate in the second residue to ethyl acetate in the second distillate approaches zero.

The weight ratio of ethanol in the second residue to second distillate preferably is at least 3:1, e.g., at least 6:1, at least 8:1, at least 10:1 or at least 15:1. All or a portion of the third residue is recycled to the second column. In one embodiment, all of the third residue may be recycled until process 100 reaches a steady state and then a portion of the third residue is recycled with the remaining being purged from the system 100. The composition of the second residue will tend to have lower amounts of ethanol than when the third residue is not recycled. As the third residue is recycled, the composition of the second residue, as provided in Table 2, comprises less than 30 wt. % of ethanol, e.g., less than 20 wt. % or less than 15 wt. %. The majority of the second residue preferably comprises water. Notwithstanding this effect, the extractive distillation step advantageously also reduces the amount of ethyl acetate that is sent to the third column, which is highly beneficial in ultimately forming a highly pure ethanol product.

As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure with respect to organic impurities and other than the azeotropic water content, as the distillate in line 119. The distillate of third column 109 preferably is refluxed as shown in FIG. 1, for example, at a reflux ratio of from 1:10 to 10:1, e.g., from 1:3 to 3:1 or from 1:2 to 2:1. The third residue in line 121, which preferably comprises primarily water, preferably is returned to the second column 108 as an extraction agent as shown in FIG. 1, and as described above. In one embodiment, a first portion of the third residue in line 121 is recycled to the second column and a second portion is purged and removed from the system. In one embodiment, once the process reaches steady state, the second portion of water to be purged is substantially similar to the amount water formed in the hydrogenation of acetic acid. In one embodiment, a portion of the third residue may be used to hydrolyze any other stream, such as one or more streams comprising ethyl acetate.

Although FIG. 1 shows third residue being directly recycled to second column 108, third residue may also be returned indirectly, for example, by storing a portion or all of the third residue in a tank (not shown) or treating the third residue to further separate any minor components such as aldehydes, higher molecular weight alcohols, or esters in one or more additional columns (not shown).

Third column 109 is preferably a tray column as described above and operates at atmospheric pressure or optionally at pressures above or below atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C. Exemplary components of the distillate and residue compositions for third column 109 are provided in Table 5 below. It should be understood that the distillate and residue may also contain other components, not listed, such as components in the feed.

TABLE 5

| THIRD COLUMN | | | |
|---|---|---|---|
| | Conc. (wt. %) | Conc. (wt. %) | Conc. (wt. %) |
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

In one embodiment, the third residue in line 121 is withdrawn from third column 109 at a temperature higher than the operating temperature of the second column 108. Preferably, the third residue in line 121 is integrated to heat one or more other streams or is reboiled prior to be returned to the second column 108.

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, distillation columns (e.g., a finishing column) or molecular sieves.

Returning to second column 108, the second distillate preferably is refluxed as shown in FIG. 1, optionally at a reflux ratio of 1:10 to 10:1, e.g., from 1:5 to 5:1 or from 1:3 to 3:1. As shown in FIG. 1, the second distillate may be purged or recycled to the reaction zone. In one embodiment, the second distillate in line 120 is further processed in a fourth column 123 as shown in FIG. 2. As indicated above in Table 4, although the second distillate in line 120 primarily comprises ethyl acetate, the ethyl acetate is not substantially pure and contains additional components. These additional components may be processed and removed from the second distillate.

The system 100 in FIG. 2 is similar to FIG. 1, with the addition that the second distillate in line 120 is fed to fourth column 123, also referred to as the "acetaldehyde removal column." In fourth column 123 the second distillate is separated into a fourth distillate, which comprises acetaldehyde, in line 124. In fourth column 123 the second distillate is separated into a fourth distillate, which comprises acetaldehyde, in line 124 and a fourth residue, which comprises ethyl acetate, in line 125. The fourth distillate preferably is refluxed at a reflux ratio of from 1:20 to 20:1, e.g., from 1:15 to 15:1 or from 1:10 to 10:1, and a portion of the fourth distillate is returned to the reaction zone 101 as shown by line 124. For example, the fourth distillate may be combined with the acetic acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the figure), the acetaldehyde may be collected and utilized, with or without further purification, to make useful products including but not limited to n-butanol, 1,3-butanediol, and/or crotonaldehyde and derivatives.

The fourth residue of fourth column 123 may be purged via line 125. The fourth residue primarily comprises ethyl acetate and ethanol, which may be suitable for use as a solvent mixture or in the production of esters. In one preferred embodiment, the acetaldehyde is removed from the second distillate in fourth column 123 such that no detectable amount of acetaldehyde is present in the residue of column 123.

Fourth column 123 is preferably a tray column as described above and preferably operates above atmospheric pressure. In one embodiment, the pressure is from 120 KPa to 5,000 KPa, e.g., from 200 KPa to 4,500 KPa, or from 400 KPa to 3,000 KPa. In a preferred embodiment the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 123 are provided in Table 6 below. It should be understood that the distillate and residue may also contain other components, not listed, such as components in the feed.

TABLE 6

FOURTH COLUMN

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0.01 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

Similar to FIG. 1, FIG. 2 also shows that the third residue in line 121 is recycled to second column 108. In one embodiment, recycling the third residue further reduces the aldehyde components in the second residue and concentrates these aldehyde components in the distillate stream 120 and thereby sent to the fourth column 123, wherein the aldehydes may be more easily separated in the fourth column 123. Such embodiments also provide a finished ethanol product that preferably has low amounts of aldehydes and esters.

Finished Ethanol

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol is from 80 to 1,000 wppm, e.g., from 95 to 1,000 wppm, from 100 to 700 wppm, or from 150 to 500 wppm. In one embodiment, the finished ethanol composition preferably is substantially free of acetaldehyde and may comprise less than 8 wppm of acetaldehyde, e.g., less than 5 wppm or less than 1 wppm.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in copending U.S. application Ser. No. 12/221,137 and U.S. application Ser. No. 12/221,138, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, an example is provided below. The following examples describe the various distillation processes of the present invention.

EXAMPLES

Example 1

A crude ethanol product comprising ethanol, acetic acid, water and ethyl acetate was produced by reacting a vaporized feed comprising 95.2 wt. % acetic acid and 4.6 wt. % water with hydrogen in the presence of a catalyst comprising 1.6 wt. % platinum and 1 wt. % tin supported on ⅛ inch calcium silicate modified silica extrudates at an average temperature of 291° C., an outlet pressure of 2,063 KPa. Unreacted hydrogen was recycled back to the inlet of the reactor such that the total $H_2$/acetic acid molar ratio was 5.8 at a GHSV of 3,893 $hr^{-1}$. Under these conditions, 42.8% of the acetic acid was converted, and the selectivity to ethanol was 87.1%, selectivity to ethyl acetate was 8.4%, and selectivity to acetaldehyde was 3.5%. The crude ethanol product was purified using a separation scheme having distillation columns as shown in FIG. 1.

The crude ethanol product was fed to the first column at a feed rate of 20 g/min. The composition of the liquid feed is provided in Table 8. The first column is a 2 inch diameter Oldershaw with 50 trays. The column was operated at a temperature of 115° C. at atmospheric pressure. Unless otherwise indicated, a column operating temperature is the temperature of the liquid in the reboiler and the pressure at the top of the column is atmospheric (approximately one atmosphere). The column differential pressure between the trays in the first column was 7.4 KPa. The first residue was withdrawn at a flow rate of 12.4 g/min and returned to the hydrogenation reactor.

The first distillate was condensed and refluxed at a 1:1 ratio at the top of the first column, and a portion of the distillate was introduced to the second column at a feed rate of 7.6 g/min. The second column is a 2 inch diameter Oldershaw design equipped with 25 trays. The second column was operated at a temperature of 82° C. at atmospheric pressure. The column differential pressure between the trays in the second column was 2.6 KPa. The second residue was withdrawn at a flow rate of 5.8 g/min and directed to the third column. The second distillate was refluxed at a ratio of 4.5:0.5 and the remaining distillate was collected for analysis. No extraction agent was fed to the second column in this example. The compositions of the feed, distillates, and residues are provided in Table 8.

TABLE 8

| | | First Column | | Second Column | |
|---|---|---|---|---|---|
| Component | Feed (wt. %) | Distillate (wt. %) | Residue (wt. %) | Distillate (wt. %) | Residue (wt. %) |
| Water | 13.8 | 24.7 | 5.6 | 5.1 | 30.8 |
| Acetaldehyde | nd | 1.8 | nd | 8.3 | nd |
| Acetic Acid | 55.0 | 0.08 | 93.8 | 0.03 | 0.1 |
| Ethanol | 23.4 | 57.6 | 0.06 | 12.4 | 67.6 |
| Ethyl Acetate | 6.5 | 15.1 | nd | 76.0 | nd |
| Acetal | 0.7 | 0.1 | nd | 0.006 | 0.03 |
| Acetone | nd | 0.01 | nd | 0.03 | nd |

Example 2

The crude ethanol product of Example 1 was processed under similar conditions, except that an extraction agent, deionized water, was fed to the second column. The molar ratio of the water in the extraction agent to the ethanol in the feed to the second column was 6.4:1. The use of an extraction agent in the second column provided for increased amounts of ethyl acetate in the distillate and decreased amounts of ethanol in the distillate as shown in Table 9. The change in the weight percent from Table 8 to Table 9 ("Distillate Δ %") with the extraction agent is also provided in Table 9.

TABLE 9

| | Second Column | | |
|---|---|---|---|
| Component | Distillate (wt. %) | Distillate Δ % | Residue (wt. %) |
| Water | 8.8 | +73.2% | 80.1 |
| Acetaldehyde | 2.2 | −73.3% | nd |
| Acetic Acid | 0.01 | −79.8% | 0.4 |
| Ethanol | 3.5 | −71.9% | 23.0 |
| Ethyl Acetate | 85.1 | +12.0% | 0.1 |
| Acetal | 0.02 | — | nd |
| Acetone | 0.003 | — | nd |

Example 3

A crude ethanol product comprising ethanol, acetic acid, water and ethyl acetate was produced by reacting a vaporized feed comprising 96.3 wt. % acetic acid and 4.3 wt. % water with hydrogen in the presence of a catalyst comprising 1.6 wt. % platinum and 1% tin supported on ⅛ inch calcium silicate modified silica extrudates at an average temperature of 290° C., an outlet pressure of 2,049 KPa. Unreacted hydrogen was recycled back to the inlet of the reactor such that the total $H_2$/acetic acid molar ratio was 10.2 at a GHSV of 1,997 $hr^{-1}$. Under these conditions, 74.5% of the acetic acid was converted, and the selectivity to ethanol was 87.9%, selectivity to ethyl acetate was 9.5%, and selectivity to acetaldehyde was 1.8%. The crude ethanol product was purified using a separation scheme having distillation columns as shown in FIG. 1.

The crude ethanol product was fed to the first column at a feed rate of 20 g/min. The composition of the liquid feed is provided in Table 10. The first column is a 2 inch diameter Oldershaw with 50 trays. The column was operated at a temperature of 116° C. at atmospheric pressure. The column differential pressure between the trays in the first column was 8.1 KPa. The first residue was withdrawn at a flow rate of 10.7 g/min and returned to the hydrogenation reactor.

The first distillate was condensed and refluxed at a 1:1 ratio at the top of the first column, and a portion of the distillate was introduced to the second column at a feed rate of 9.2 g/min. The second column is a 2 inch diameter Oldershaw design equipped with 25 trays. The second column was operated at a temperature of 82° C. at atmospheric pressure. The column differential pressure between the trays in the second column was 2.4 KPa. The second residue was withdrawn at a flow rate of 7.1 g/min and directed to the third column. The second distillate was refluxed at a ratio of 4.5:0.5 and the remaining distillate was collected for analysis. No extraction agent was fed to the second column in this example. The compositions of the feed, distillates, and residues are provided in Table 10.

TABLE 10

| | | First Column | | Second Column | |
|---|---|---|---|---|---|
| Component | Feed (wt. %) | Distillate (wt. %) | Residue (wt. %) | Distillate (wt. %) | Residue (wt. %) |
| Water | 14.6 | 27.2 | 3.7 | 3.0 | 36.2 |
| Acetaldehyde | nd | 1.5 | nd | 10.3 | nd |
| Acetic Acid | 49.1 | 0.2 | 98.2 | 0.04 | 0.3 |
| Ethanol | 27.6 | 54.5 | 0.04 | 13.3 | 64.4 |
| Ethyl Acetate | 7.9 | 15.2 | nd | 75.7 | 1.8 |
| Acetal | 0.7 | 0.1 | nd | 0.01 | 0.02 |
| Acetone | nd | 0.01 | nd | 0.03 | nd |

Example 4

The crude ethanol product of Example 2 was processed under similar conditions, except that an extraction agent, deionized water, was fed to the second column. The molar ratio of the water in the extraction agent to the ethanol in the feed to the second column was 4:1. The use of an extraction agent in the second column provided for increased amounts of ethyl acetate in the distillate and decreased amounts of ethanol in the distillate as shown in Table 11. The change in the weight percent from Table 10 to Table 11 ("Distillate Δ %") with the extraction agent is also provided in Table 11.

TABLE 11

| | Second Column | | |
|---|---|---|---|
| Component | Distillate (wt. %) | Distillate Δ % | Residue (wt. %) |
| Water | 8.8 | +197.2% | 71.2 |
| Acetaldehyde | 6.4 | −37.9% | nd |
| Acetic Acid | 0.04 | — | 0.2 |
| Ethanol | 4.5 | −66.0% | 32.0 |
| Ethyl Acetate | 77.6 | +2.5% | 0.004 |
| Acetal | — | — | nd |
| Acetone | — | — | nd |

FIG. 3 is a graph of the ethanol and ethyl acetate concentration changes in the second distillate achieved by varying the mole ratio of water in the extraction agent to ethanol in feed directed to the second column. The concentrations of ethanol and ethyl acetate are normalized in FIG. 3 to a common "water-free" basis for comparison purposes.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for purifying a crude ethanol product, the process comprising the steps of:
   hydrogenating an acetic acid feed stream in the presence of a catalyst to form a crude ethanol product;
   separating at least a portion of the crude ethanol product in a first column into a first distillate comprising ethanol, water and ethyl acetate, and a first residue comprising acetic acid; and
   recovering ethanol from the first distillate in one or more distillation columns
   wherein one of the one or more distillation columns is an extractive distillation column.

2. The process of claim 1, wherein an extractive agent is fed to the extractive distillation column.

3. The process of claim 2, wherein the extractive agent is water.

4. The process of claim 1, wherein the first distillate is separated in an extractive distillation column to form a second distillate comprising ethyl acetate and a second residue comprising ethanol and water.

5. The process of claim 4, wherein at least a portion of the second residue is further separated in a third distillation column to form a third distillate comprising ethanol and a third residue comprising water.

6. The process of claim 4, wherein an extractive agent comprising water is fed to the extractive distillation column.

7. The process of claim 6, wherein the water is from an external source.

8. The process of claim 6, wherein at least a portion of the water is from an external source and at least a portion of the water is from the third residue.

9. The process of claim 6, wherein the molar ratio of water in the extraction agent to ethanol in the portion of the first distillate is at least 0.5:1.

10. The process of claim 6, wherein the molar ratio of water in the extraction agent to ethanol in the portion of the first distillate is at least 4:1.

11. A process for recovering ethanol, comprising:
    hydrogenating an acetic acid feed stream in the presence of a catalyst to form a crude ethanol product;
    separating at least a portion of the crude ethanol product in a first column into a first distillate comprising ethanol, water, and ethyl acetate, and a first residue comprising acetic acid, based on the total weight of the first residue;
    separating at least a portion of the first distillate in a second column into a second distillate comprising ethyl acetate and a second residue comprising ethanol and water;
    separating at least a portion of the second residue in a third column into a third distillate comprising ethanol and a third residue comprising water; and
    recovering ethanol from the third distillate;
    wherein the second column is an extractive distillation column and water is used as an extractive agent.

12. The process of claim 11, wherein the water is from an external source.

13. The process of claim 11, wherein at least a portion of the water is from an external source and at least a portion of the water is from the third residue.

14. The process of claim 11, wherein the molar ratio of water in the extraction agent to ethanol in the portion of the first distillate is at least 0.5:1.

15. The process of claim 11, wherein the molar ratio of water in the extraction agent to ethanol in the portion of the first distillate is at least 4:1.

16. A process for purifying a crude ethanol product, the process comprising the steps of:
    hydrogenating an acetic acid feed stream in the presence of a catalyst to form a crude ethanol product comprising ethanol, acetic acid and ethyl acetate;
    esterifying the crude ethanol product to form an ethyl acetate stream comprising ethyl acetate, water and ethanol;
    extracting ethanol from ethyl acetate using an extractive agent; and
    recovering ethanol.

17. The process of claim 16, wherein the extractive agent comprises water and wherein the water is from an external source.

18. The process of claim 17, wherein the extracting step is conducted at a molar ratio of water in the extraction agent to ethanol in the portion of the ethyl acetate stream that is at least 0.5:1.

19. The process of claim 17, wherein the extracting step is conducted at a molar ratio of water in the extraction agent to ethanol in the portion of the ethyl acetate stream that is at least 4:1.

20. The process of claim 16, wherein the extracting is performed in an extractive distillation column.

* * * * *